(12) United States Patent
Czarnik et al.

(10) Patent No.: US 6,279,603 B1
(45) Date of Patent: Aug. 28, 2001

(54) FLUID-COOLED INJECTOR

(75) Inventors: Richard J. Czarnik, Easthampton; Jeffrey P. DiCarlo, Holyoke, both of MA (US); Curtis J. Knapper, New Fairfield, CT (US); Thomas C. Simard, Agawam, MA (US); Theodore J. Tarabulski, Brewster, NY (US)

(73) Assignees: Ambac International, West Springfield, MA (US); Clean Diesel Technologies, Inc., Stamford, CT (US)

( * ) Notice: Subject to any disclaimer, the term of this patent is extended or adjusted under 35 U.S.C. 154(b) by 0 days.

(21) Appl. No.: 09/164,304

(22) Filed: Oct. 1, 1998

(51) Int. Cl.$^7$ .................................................. F16K 49/00
(52) U.S. Cl. .......................... 137/339; 60/274; 123/472; 137/340; 239/125; 251/129.15; 422/177
(58) Field of Search ................................. 60/274; 123/461, 123/470, 472; 422/177, 180; 239/87, 88, 89, 90, 91, 93, 95, 99, 106, 110, 124, 125, 132, 132.5; 251/318, 324, 325, 129.15; 137/340, 339

(56) References Cited

U.S. PATENT DOCUMENTS

| | | | |
|---|---|---|---|
| 2,540,663 | * 2/1951 | Garey | 239/462 |
| 3,680,537 | * 8/1972 | Suda et al. | 123/472 |
| 5,522,218 | * 6/1996 | Lane et al. | 60/274 |

* cited by examiner

Primary Examiner—Marian C. Knode
Assistant Examiner—Frederick Varcoe
(74) Attorney, Agent, or Firm—Synnestvedt & Lechner LLP

(57) ABSTRACT

An injector for delivery of a fluid into a stream of hot gas is disclosed. The injector has a valve body with an elongated chamber in fluid communication with an orifice. A valve seat surrounds the orifice. A valve plunger is disposed within the chamber, an end of the plunger being adapted to sealingly interengage the seat. The plunger is slidably movable between an open and a closed position to open and close the orifice. A fluid inlet and an outlet are disposed within the valve body to deliver fluid to an annular fluid passageway in the chamber adjacent to the valve seat. Fluid is circulated through the annular passageway to cool the valve and a portion of the fluid is expelled through the orifice when the orifice is opened. The plunger is biased into the closed position by a coil spring and movable into the open position by a solenoid actuator mounted atop the valve body. The injector is mounted on an exhaust conduit of an internal combustion engine with the orifice in fluid communication with the exhaust gases. A heat shield surrounding the orifice is interposed between the exhaust gases and the valve body, a radiant heat reflector is positioned between exposed parts of the injector and the exhaust conduit, and an atomizing hook is positioned in a spaced apart relation facing the orifice to control the dispersion characteristics of the expelled fluid.

10 Claims, 2 Drawing Sheets

FLUID-COOLED INJECTOR

FIELD OF INVENTION

This invention relates to injectors and especially to fluid-cooled injectors wherein the fluid is a liquid reagent and a portion of the reagent is injected as an atomized liquid reagent into the exhaust gas stream of an internal combustion engine.

BACKGROUND OF INVENTION

Improved fuel efficiency for vehicles having internal combustion engines can be achieved by using diesel engines or gasoline engines operated with an excess of oxygen over the amount necessary for complete combustion of the fuel. Such engines are said to run "lean" or on a "lean mixture." The increase in fuel economy, however, is offset by undesired pollution emissions, specifically in the form of oxides of nitrogen (NOx).

One method used to reduce NOx emissions from internal combustion engines is known as selective catalytic reduction (SCR). SCR, when used, for example, to reduce NOx emissions from a diesel engine, involves injecting an atomized reagent into the exhaust stream of the engine in relation to one or more selected engine operational parameters, such as exhaust gas temperature, engine rpm or engine load as measured by engine fuel flow, turbo boost pressure or exhaust NOx mass flow. The reagent/exhaust gas mixture is passed through a reactor containing a catalyst, such as, for example, activated carbon, or metals, such as platinum, vanadium or tungsten, which are capable of reducing the NOx concentration in the presence of the reagent. An SCR system of this type is disclosed in U.S. patent application Ser. No. 08/1831,209, issued as U.S. Pat. No. 5,976,475 hereby incorporated by reference.

An aqueous solution of urea is known to be an effective reagent in SCR systems for diesel engines but suffers several disadvantages. Urea is highly corrosive and tends to attack mechanical components of the SCR system, such as the injectors used to inject the urea mixture into the exhaust gas stream. Urea also tends to solidify upon prolonged exposure to elevated temperatures, such as encountered in diesel exhaust systems. Solidified urea tends to accumulate in the narrow passageways and orifice openings typically found in injectors. The solidified urea fouls moving parts of the injector and clogs any openings, thus, rendering the injector unusable.

Furthermore, if the urea mixture is not finely atomized, urea deposits will form in the catalytic reactor, inhibiting the action of the catalyst and thereby reducing the SCR system effectiveness. High injection pressures are one way of dealing with the problem of insufficient atomization of the urea mixture, but high injection pressures often result in over-penetration of the injector spray plume into the exhaust stream, causing the plume to impinge on the inner surface of the exhaust pipe opposite the injector. Over-penetration leads to inefficient use of the urea mixture and reduces the range over which the vehicle can operate with reduced NOx emissions. Like fuel for the vehicle, only a finite amount of aqueous urea can be carried and what is carried should be used efficiently to maximize vehicle range and reduce the need for frequent fill ups of the reagent.

Additionally, aqueous urea is a poor lubricant. This characteristic adversely affects moving parts within the injector and requires that special fits, clearances and tolerances be employed between relatively moving parts within an injector.

SUMMARY AND OBJECTS OF INVENTION

The invention provides an injector for delivery of a fluid into a stream of hot gas, the injector being designed to operate effectively with a corrosive, temperature-sensitive reagent, such as aqueous urea. When used in a system for reducing NOx emissions, the injector is mounted on an exhaust conduit of an internal combustion engine where it injects the reagent into the exhaust gas stream.

The injector comprises a valve and a means for actuating the valve between a closed position and an open position. Acceptable actuating means include, for example, a solenoid-type actuator. Preferably the components of the valve exposed to extreme heat or corrosive reagents like urea are made of a corrosion resistant material such as stainless steel.

The valve includes an orifice through which the reagent is expelled when the valve is in the open position. Regardless of the state of the valve (i.e., open or closed), the reagent is continuously circulated through it when the system is in operation, at least a portion of the circulating reagent being expelled when the valve is opened. The circulation of the reagent cools the valve and minimizes the dwell time of the reagent within the valve, thereby minimizing exposure of the reagent to heat and the creation of urea deposits. Thus, aqueous urea, for example, can be effectively used with such an injector without the characteristic fouling and clogging of the injector. Means independent of the valve actuating means are provided for continuously circulating the reagent through the valve, as described in detail below.

Preferably the valve comprises a valve body which has an elongated cylindrical chamber therein in fluid communication with the orifice. A valve seat is positioned within the chamber surrounding the orifice. An elongated valve plunger is slidably mounted within the chamber. One end of the plunger is sealingly interengagable with the valve seat to close the orifice. The plunger is connected with the actuating means and is movable from the closed position where the plunger end sealingly engages the valve seat and the open position where the plunger end is removed from sealing interengagement with the valve seat to open the orifice.

The means for independently circulating fluid through the valve comprises a portion of the plunger which is arranged adjacent to the plunger end. This portion of the plunger has a diameter less than the chamber diameter and forms an annular fluid space or passageway within the valve adjacent to the valve seat and the orifice. The annular passageway, thus, allows for both the continuous circulation of fluid through the valve and the expelling of a portion of the fluid through the orifice when the valve is in the open position.

Preferably, the independent fluid circulating means further comprises a fluid inlet and a fluid outlet arranged within the valve body in fluid communication with the annular passageway. Fluid, such as the aqueous urea reagent, is supplied from a reservoir and flows into the valve through the inlet, continues through the annular passageway and exits the valve via the outlet, thereby cooling the injector. When the valve is opened by the actuator, the valve plunger is moved to the open position, and a portion of the fluid is expelled from the chamber through the orifice.

In order to provide additional heat protection for the injector, a heat shield is preferably interposed between the valve and the stream of hot gas. The heat shield has an aperture which is aligned with the orifice. The heat shield aperture allows fluid expelled from the valve to pass through the heat shield and into the hot gas stream. The heat shield preferably comprises a metal plate and a layer of insulating material interposed between the plate and the valve. The heat shield aperture passes through both the layer of insulating material, as well as the metal plate.

To improve atomization of liquid reagents, especially at relatively low injection pressures, an atomizing hook is preferably mounted on the valve. The atomizing hook has an end surface which is positioned in a spaced apart relation with the orifice. Liquid reagent expelled through the orifice impinges on the hook end surface where further atomization of the reagent occurs. The shape and position of the hook end surface directly affect the dispersion characteristics of the injected reagent.

It is an object of the invention to provide an injector for injecting a fluid into a stream of hot gas.

It is another object of the invention to provide an injector useable with corrosive liquids such as aqueous urea.

It is yet another object of the invention to provide an injector in which aqueous urea will not solidify when the injector is exposed to heat.

It is still another object of the invention to provide an injector which achieves fine atomization of liquid reagents at relatively low injection pressures.

It is a further object of the invention to provide an injector wherein a portion of the fluid being injected is also continuously circulated through the injector to cool the injector.

It is yet a further object of the invention to provide an injector wherein the dwell time of the fluid within the injector is minimized.

It is still a further object of the invention to provide an injector useable in a pollution control system for reducing NOx emissions of internal combustion engines.

These and other objects will become apparent from a consideration of the following drawings and detailed description of the invention.

DETAILED DESCRIPTION OF THE PREFERRED EMBODIMENT

Figure 1:
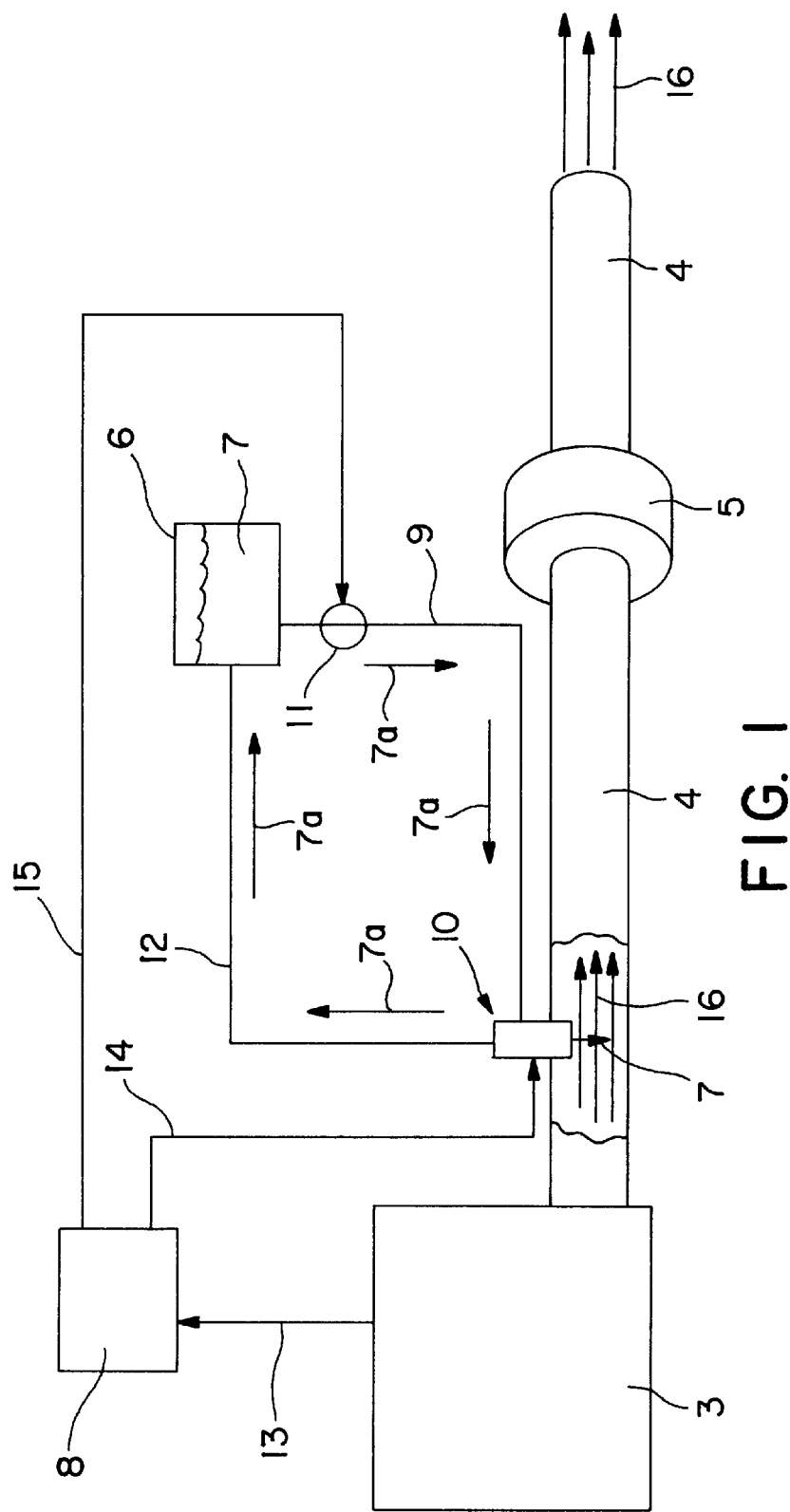
FIG. 1 shows a schematic diagram of a pollution emission control system using an injector according to the invention.

FIG. 1 illustrates a pollution control system as might be used to reduce NOx emissions from the exhaust of a diesel engine 3. The system includes an engine exhaust conduit 4 in fluid communication with a catalytic reactor 5, a reagent reservoir 6 holding reagent 7, a central processing unit 8 and an injector 10. Injector 10 is mounted on exhaust conduit 4 and fed reagent, for example, a solution of aqueous urea via supply line 9 extending from reservoir 7 to the injector. A pump 11 is used to pump the reagent to the injector at a predetermined pressure. Reagent 7 is circulated back to the reservoir via return line 12, the circulation of the reagent being shown by the arrows 7a.

In operation, signals 13, representing engine operational parameters such as exhaust gas temperature, engine speed and fuel flow rate are monitored by central processing unit 8. In response to these signals and preprogrammed algorithms, central processing unit 8 sends control signals 14 and 15 to injector 10 and pump 11 respectively, the control signals commanding pump 11 to circulate reagent and injector 10 to inject or cease injecting reagent into exhaust gases 16 within the exhaust conduit 4. The reagent is atomized upon injection into the conduit and forms a mixture with the exhaust gases. This mixture enters the catalytic reactor 5 which contains a catalyst, such as activated carbon, or metals, such as platinum, tungsten or vanadium, which reduces NOx in the exhaust gases in the presence of the reagent. The exhaust exits the conduit 4 and passes to the atmosphere.

During system operation, regardless of whether or not the injector is releasing reagent into the exhaust gases 16, reagent 7 is circulated continuously between the reservoir 6 and the injector 10 to cool the injector and minimize the dwell time of the reagent in the injector so that the reagent remains cool. Continuous reagent circulation is necessary for temperature-sensitive reagents, such as aqueous urea, which tend to solidify upon exposure to elevated temperatures of 300° C. to 650° C. as would be experienced in an engine exhaust system. It has been found to be important to keep the urea mixture below 140° C. and preferably in a lower operating range between 5° C. and 95° C. to provide a margin of safety ensuring that solidification of the urea is prevented. Solidified urea, if allowed to form, would foul the moving parts and openings of the injector, eventually rendering the injector useless. In the case of a 310-horsepower diesel engine with a baseline NOx emissions level of 8 grams/bHp-hr at full load, circulation rates of aqueous urea between 0.5 gallons per minute and 0.75 gallons per minute through an injector according to the invention have been found to effectively cool the aqueous urea and prevent solidification. It will be recognized that flow rates will depend on engine size and NOx levels. It is an advantage of the invention that more concentrated solutions can be utilized, i.e., 25–35%, because throughout the system, the solution is not subject to conditions which would cause significant hydrolysis or solubility problems.

Figure 2:
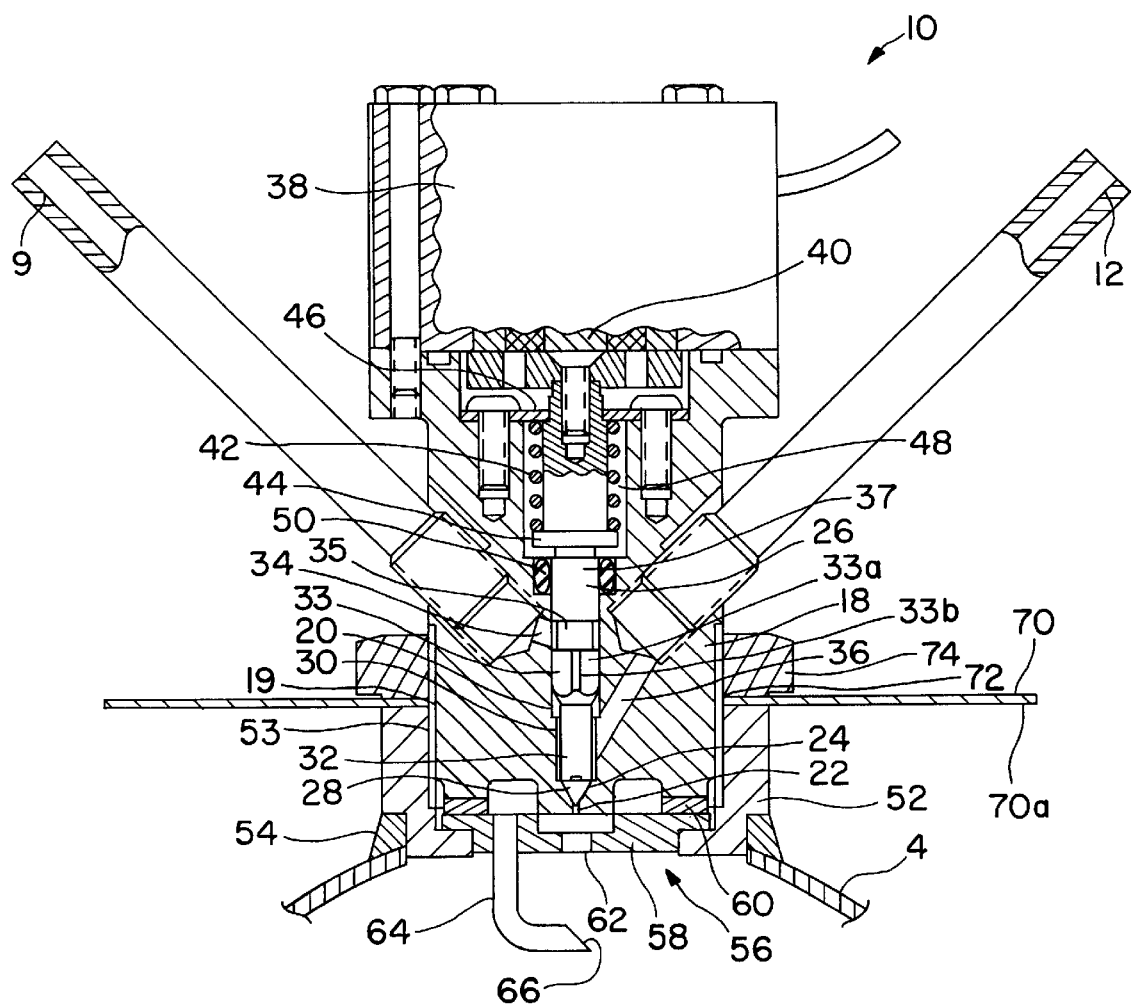
FIG. 2 shows a longitudinal cross-sectional view of an injector according to the invention.

FIG. 2 shows a cross-sectional view of the preferred embodiment of the injector 10 according to the invention. The injector is shown mounted on an exhaust gas conduit 4, only partially depicted, in cross-section. Injector 10 comprises a valve body 18 having an elongated cylindrical chamber 20 disposed therein. Chamber 20 is in fluid communication with an orifice 22 which opens onto the exhaust gases within conduit 4. Surrounding orifice 22 is a valve seat 24 which can have any practical shape but is preferably conical. A valve member in the form of an elongated valve plunger 26 is slidably mounted within chamber 20. Valve plunger 26 has an end 28 formed to sealingly interengage valve seat 24, as seen in FIG. 2, thereby closing orifice 22 from fluid communication with chamber 20.

Valve plunger 26 is movable within the chamber between the closed position shown in FIG. 2 and an open position wherein end 28 is removed from sealing interengagment with valve seat 24. In the open position, orifice 22 is opened to fluid communication with chamber 20.

Together the chamber 20 and the valve plunger 26 provide a means for circulating fluid, such as the reagent, through the valve for cooling the valve and for minimizing the dwell time of the reagent within the valve. The circulating means comprises an annular fluid passageway 30 formed between the relatively larger inner diameter of chamber 20 and the relatively smaller outer diameter of a section 32 of the valve plunger 26. Preferably, plunger section 32 is arranged adjacent to plunger end 28 and close to valve seat 24 and orifice 22. Positioning fluid passageway 30 close to the orifice allows the circulating fluid to directly cool an otherwise hot part of the valve body most sensitive to the adverse effects of heat. Thus, for example, aqueous urea, when used with this cooled valve, will not solidify anywhere within chamber 20. If allowed to solidify, the urea could prevent plunger 26 from seating properly or could cause the plunger to seize in either the open or closed position and/or the orifice 22 could become clogged. By directly cooling this region of the valve, however, the detrimental effects of elevated temperature on the reagent, the moving parts, and the openings of the valve are avoided.

As seen in FIG. 2, plunger 26 further comprises a guide section 33 disposed adjacent to section 32 of the valve plunger. Guide section 33 preferably has a polygonal cross-section formed by a plurality of flats 33a intersecting at a plurality of corners 33b. Flats 33a provide fluid circulation spaces adjacent to the chamber 20 and augment the cooling function of the fluid passageway 30. The flats also provide space for any debris formed within or brought into chamber 20 to wash out of the chamber with the circulating fluid.

The corners 33b of the guide section 33 provide a stabilizing and a guiding function for plunger 26. The corners are toleranced to ride close to or in light contact with the wall of chamber 20 to provide support points which guide the plunger within the chamber to ensure proper seating of plunger end 28.

Immediately above guide section 33 is a reduced circular cross-section 35 of plunger 26. Reduced section 35 provides an annular space for fluid to flow into the chamber through an inlet, described in detail below. Above the reduced section is a circular guide section 37. Circular guide section 37 provides the main guiding function for sliding motion of the plunger 26 within the chamber 20. The tolerance between the circular guide section and the chamber is sufficient to allow relative motion and lubrication of the plunger while still guiding the plunger's motion and forming a partial hydraulic seal between the plunger and the chamber.

Generally the specific tolerances required at the various sections between the valve plunger and the chamber will vary according to the operating temperature, operating pressure, the desired flow rate and circulation rate of the reagent, the tribological properties of the reagent and the materials chosen for the valve plunger and valve body. The tolerances for optimum injector performance are best obtained experimentally by a few field trials.

The cooling fluid is delivered to the annular fluid passageway 30 through fluid inlet 34. Fluid inlet 34 is arranged within valve body 18 in fluid communication with chamber 20 and is externally connected to supply line 9 (FIG. 1). It is preferred that the fluid inlet be positioned to deliver fluid to chamber 20 in a region removed from the valve seat 24 adjacent to reduced section 25 and guide section 33, as shown in FIG. 2. Positioning the fluid inlet upstream from the seat, as shown, allows the fluid to contact valve plunger 26 over a substantial length before it encounters the valve seat, thereby enhancing the cooling function of the fluid. Fluid, such as reagent 7, is pumped via pump 11 at a predetermined pressure into the fluid inlet 34 from which it flows along valve plunger 26 into annular fluid passageway 30.

A fluid outlet 36 is provided to remove the fluid from the annular fluid passageway. Fluid outlet 36 is arranged within valve body 18 in fluid communication with chamber 20. Preferably, fluid outlet 36 is positioned as shown in FIG. 2 for removing fluid from chamber 20 in the region of the valve seat 24. Fluid outlet 36 is externally connected to return line 12 (FIG. 1), thus permitting the fluid (such as reagent 7) to circulate from reservoir 6, through supply line 9, through fluid inlet 34, into annular fluid passageway 30, through fluid outlet 36, through return line 12 and back into reservoir 6. This circulation keeps critical regions of the valve body 18 cool and minimizes the dwell time of the fluid in the injector.

When the valve plunger 26 is moved from the closed position, shown in FIG. 2, to an open position, plunger end 28 is removed from sealing interengagement with seat 24. This action opens orifice 22 and allows at least a portion of the circulating fluid to be expelled through the orifice and into exhaust conduit 4. To effect the opening and closing of the orifice, actuating means are provided, preferably in the form of solenoid 38 mounted atop valve body 18. Solenoid 38 has an armature 40 connected to valve plunger 26. When the solenoid is energized, the armature 40 is drawn upward, thereby sliding valve plunger 26 within chamber 20 from the closed position to the open position. The solenoid would be energized, for example, in response to a signal 14 (see FIG. 1) from central processing unit 8, which decides, based upon sensor input signals 13 and its preprogrammed algorithms, when reagent is needed for effective selective catalytic reduction of NOx emissions in the exhaust stream.

As seen in FIG. 2, valve plunger 26 is biased in the closed position by a biasing member, preferably in the form of a coil spring 42 coaxially disposed about valve plunger 26. The valve plunger has a shoulder 44 which serves as a lower spring seat against which the spring can push to bias the valve plunger. An upper plate 46 is fixed to the valve body 18 and serves as the upper spring seat, as well as a stop to limit the upward travel of the valve plunger.

Spring 42 is located within a spring chamber 48 which is isolated from chamber 20 by seal 50. Seal 50 is preferably made of carbon reinforced Teflon® or glass reinforced Teflon® and prevents any corrosive reagent from entering the spring chamber and possibly attacking or fouling the spring and the solenoid.

Figure 3:
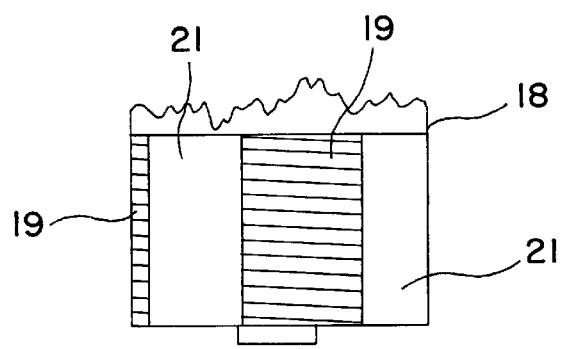
FIG. 3 shows a side view of the valve body of the injector according to the invention.

Injector 10 is shown mounted on exhaust conduit 4 by means of sleeve 52 which is welded to an opening in the conduit by weldment 54. Preferably, valve body 18 has external threads 19 which engage matching internal threads 53 in sleeve 52 to attach the injector to the sleeve. In order to minimize conductive heat transfer between the sleeve and the valve body, the external threads 19 are not continuous around the circumference of valve body 18 but interrupted or discontinuous, as seen in FIG. 3. Preferably, the thread contact area is minimized by using intermittent arcs of threads subtending angles on the order of 20° arranged circumferentially around valve body 18, with flat regions 21 arranged between each thread arc. The flats have an across-the-flat dimension which is less than the root diameter of the thread on valve body 18 and, therefore, make no contact with sleeve 52.

In the configuration shown, hot exhaust gases within the conduit are prevented from impinging directly upon the valve body 18 by the interposition of a heat shield 56 between the valve body and the exhaust gases. Heat shield 56 includes an outer metal plate 58 and a layer of insulating material in the form of a thermal gasket 60 interposed between outer plate 58 and valve body 18. Preferably outer plate 58 is made of stainless steel to resist the corrosive environment within the exhaust conduit. Gasket 60 is preferably made of a flexible graphite foil material whose low thermal conductivity serves to isolate valve body 18 from outer plate 58, reducing conductive heat transfer to the injector and thereby helping to keep the fluid circulating within the valve cool.

Heat shield 56 surrounds the orifice 22 and has an aperture 62 which passes through both the outer plate and the insulating thermal gasket and permits fluid expelled from the injector to pass through the heat shield and into the conduit. The heat shield has a substantially planar surface which is preferably oriented perpendicular to the jet of fluid expelled from the injector.

Further thermal protection for the injector is provided by a radiant heat reflector 70 seen edge on in FIG. 2. Reflector 70 is preferably a round disc of polished aluminum having an outer diameter of sufficient extent such that the surface 70a of the disc blocks radiant heat transfer from exhaust conduit 4 to parts of the injector which have a direct line of sight to the conduit. The reflector has a centrally positioned aperture 72 which fits around valve body 18 and sits atop sleeve 52 to mount the reflector between the exposed parts of the injector and the conduit 4. Reflector 70 is retained in position by a nut 74 which threads onto valve body 18.

It is desired to keep the injection pressure relatively low to prevent the fluid jet or plume from the injector from over-penetrating into the exhaust gas stream and impinging on the sidewall of the conduit. Injection pressures within a range of 30 to 100 psi have been found to prevent over-penetration. An injection pressure of 67 psi is preferred for the injector according to the invention.

However, lower injection pressures might not atomize the injected fluid to a sufficiently fine size for effective catalytic reduction of the NOx. To assist dispersion and atomization of the fluid within the conduit and yet maintain reasonably low injection pressures an atomization hook 64 is provided. It is an advantage of the invention that no secondary atomization fluid is required.

Hook 64 is mounted on the valve, preferably on the metal plate 58 of heat shield 56 as seen in FIG. 2. Preferably, the hook is made of stainless steel to withstand the corrosive environment within the exhaust conduit. Mounting the hook on the heat shield serves to thermally isolate the hook from the valve body 18. Because the hook extends into the exhaust stream, it will be hot, and being metal, it will tend to conduct heat readily. However, by mounting the hook on the heat shield heat conducted by the hook will be blocked by the thermal gasket 60, and heat transfer from the hook to the valve body will be minimized by this preferred mounting of the hook 64.

Hook 64 has an end surface 66 which is positioned in a spaced-apart relation facing orifice 22. When the valve plunger 26 is actuated into its open position by solenoid 38, expelling fluid at a predetermined pressure from orifice 22, the fluid jet will impinge on end surface 66. This impingement will cause further atomization of the fluid. The dispersion characteristics of the fluid are a function of the shape of the end surface, which is tuned to a particular size and shape of the exhaust stream to ensure maximum dispersion and penetration of the fluid without over-penetration.

An injector wherein critical valve components are directly cooled by circulating fluid according to the invention provides a component for a pollution control system which allows a corrosive and heat-sensitive reagent, such as aqueous urea, to be effectively employed to reduce NOx emissions and thereby ultimately attain greater fuel efficiency without the adverse effects of increased undesired emissions.

What is claimed is:

1. A fluid cooled injector comprising:

a valve body having a chamber arranged therein;

an orifice located in said valve body at a first end of said chamber;

a valve seat positioned within said chamber surrounding said orifice;

a valve member arranged within said chamber and being sealingly interengagable with said valve seat to close said orifice, said valve member being movable between a closed position wherein said valve member sealingly interengages said valve seat, and an open position, wherein said valve member is removed from interengagement with said valve seat to open said orifice;

an actuator mounted on said valve body and connected to said valve member for moving said valve member between said closed and open positions;

a fluid inlet and a fluid outlet extending through said valve body and communicating with said chamber, said fluid outlet intersecting said chamber at a position adjacent to said valve seat; and said inlet and said outlet providing a flow path for fluid through said chamber independent of the position of said valve member, thereby cooling said injector, a portion of the fluid being released from said chamber through said orifice when said valve member is in said open position.

2. An injector according to claim 1, further comprising a heat shield surrounding said orifice, said heat shield having an aperture therethrough aligned with said orifice, thereby allowing fluid released from said chamber to pass through said heat shield.

3. An injector according to claim 2, wherein said heat shield comprises a metal plate surrounding said orifice and defining said aperture, said heat shield further comprising a layer of insulating material interposed between said plate and said valve body, said aperture passing through said insulating material layer.

4. An injector according to claim 1, further comprising an atomizing hook mounted on said valve body and having an end surface positioned in a spaced apart relation facing said orifice, said end surface being located within a path of the fluid released from said injector through said orifice for controlling dispersion characteristics of the fluid.

5. An injector according to claim 4, wherein said fluid inlet intersects said chamber at a position removed from said valve seat.

6. An injector according to claim 1 wherein said chamber has a cylindrical bore having a first diameter and said valve member comprises an elongated cylindrical plunger comprising:

a first plunger portion having a diameter of a dimension allowing for slidable motion of said plunger with said bore;

a second plunger portion extending coaxially from said first plunger portion toward said valve seat and having a diameter less than said first diameter thereby forming an annular fluid circulating space within said chamber adjacent to said valve seat, at least one of said fluid inlet and said fluid outlet intersecting said chamber at said annular space;

said second plunger portion having a coaxially disposed seat portion for interengagement with said valve seat, said plunger being slidably movable within said chamber between said closed position, wherein said seat portion sealingly interengages said valve seat to close said orifice, and said open position wherein said seat portion is removed from sealing interengagement with said valve seat to open said orifice.

7. An injector according to claim 1, wherein said valve body and said valve member are made of stainless steel.

8. An injector according to claim 6, further comprising a biasing member located within said valve body for biasing said plunger into said closed position.

9. An injector according to claim 8, wherein said actuator comprises a solenoid having an armature attached to said first plunger portion, said solenoid armature effecting sliding motion of said plunger against said biasing member when said solenoid is energized and thereby moving said plunger from said closed to said open position within said chamber and means for energizing said solenoid to release the portion of the fluid from said chamber through said orifice.

10. An injector according to claim 9, wherein said biasing member comprises a coil spring coaxially arranged with said plunger.

* * * * *

UNITED STATES PATENT AND TRADEMARK OFFICE
CERTIFICATE OF CORRECTION

PATENT NO.    : 6,279,603 B1                                      Page 1 of 1
DATED         : August 28, 2001
INVENTOR(S)   : Czarnik et al.

It is certified that error appears in the above-identified patent and that said Letters Patent is hereby corrected as shown below:

<u>Column 8,</u>
Line 40, change "claim 4" to -- claim 1 --.

Signed and Sealed this

Fourteenth Day of May, 2002

*Attest:*

JAMES E. ROGAN
*Attesting Officer*     *Director of the United States Patent and Trademark Office*